(12) United States Patent
Prichep

(10) Patent No.: US 7,986,991 B2
(45) Date of Patent: *Jul. 26, 2011

(54) SYSTEM AND METHOD FOR PREDICTION OF COGNITIVE DECLINE

(75) Inventor: Leslie S. Prichep, Mamaroneck, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/639,680

(22) Filed: Dec. 16, 2009

(65) Prior Publication Data

US 2010/0094155 A1    Apr. 15, 2010

Related U.S. Application Data

(63) Continuation of application No. 11/262,906, filed on Oct. 31, 2005, now Pat. No. 7,647,098.

(51) Int. Cl.
*A61B 5/04* (2006.01)
(52) U.S. Cl. .................................................... 600/544
(58) Field of Classification Search .................. 600/300, 600/544
See application file for complete search history.

(56) References Cited

U.S. PATENT DOCUMENTS

2001/0020137 A1   9/2001   Granger
2004/0059241 A1   3/2004   Suffin

OTHER PUBLICATIONS

Prichep et al., "Prediction of Longitudinal Cognitive Decline in Normal Elderly with Subjective Complaints Using Electrophysiological Imaging", Neurobiology of Aging, Tarrytown, NY, vol. 27, No. 3, Oct. 6, 2005, XP024993041, pp. 471-481.
John, "Principles of Neurometrics" American Journal of EEG Technology, American Society of EEG Technologists, Phoenix, US, vol. 30, No. 4, Dec. 1, 1990, XP 008044680, pp. 251-266.
Pricehp et al., "Prediction of Longitudinal Cognitive Decline in Normal Elderly with Subjective Complaints Using Electrophysiological Imaging" [Online], Aug. 19, 2010, XP002597238, pp. 1.

*Primary Examiner* — Patricia C Mallari
*Assistant Examiner* — Christian Jang
(74) *Attorney, Agent, or Firm* — Fay Kaplun & Marcin, LLP

(57) ABSTRACT

A system and method for prediction of cognitive decline, comprises an input receiving input data corresponding to brain activity of an individual and a processor coupled to the input for analyzing the input data to obtain a selected set of features, the processor comparing the selected set of features to at least a portion of entries in a database corresponding to brain activity of a plurality of individuals, wherein entries in the database have been separated into a plurality of categories corresponding to one of a degree of cognitive decline and a propensity for future cognitive decline of individuals relating to the entries, the processor determining, based on the comparison, a category most closely corresponding to the selected set of features.

30 Claims, 4 Drawing Sheets

SYSTEM AND METHOD FOR PREDICTION OF COGNITIVE DECLINE

PRIORITY CLAIM

This application is a Continuation application of U.S. patent application Ser. No. 11/262,906 filed on Oct. 31, 2005 entitled System and Method for Prediction of Cognitive Decline", The entire disclosure of the prior application is considered as being part of the disclosure of the accompanying application and hereby expressly incorporated by reference herein.

FIELD OF INVENTION

The present invention relates to quantitative electroencephalographic, magnetoencephalographic and sensory event-related methods for measurement of brain activity related to cognitive functioning and, more particularly, to methods for predicting the future occurrence and evolution of cognitive decline.

BACKGROUND INFORMATION

Systems and methods exist to measure electrical activity and detect brain abnormalities based on the measured activity. An electroencephalogram ("EEG") detects electrical activity of the brain using electrodes placed on or near an individual's scalp and forehead. The EEG typically measures brain wave activity across a range of frequencies, from one or an array of electrodes placed at standardized locations on the head or scalp and forehead. For example, 19 different sites are often used to detect the activity of underlying regions of the brain. The most common method to define these sites is called the International 10/20 Electrode Placement System, but other positions may be selected.

Quantitative EEG ("qEEG") involves digital analysis of the EEG data, usually represented as a frequency spectrum evaluating the amount of activity of detected signals at the various frequencies represented in the EEG data Normative values as a function of age have been established for the activity spectrum characteristics for each electrode position and are known to have high sensitivity and specificity to abnormality and to be independent of race, socio-economic status or ethnicity. Deviations from these normative values may be used to identify profiles of abnormalities which can describe different categories of brain dysfunction. Studies utilizing qEEG have reported a clear relationship between the degree of cognitive decline in aging persons and the magnitude of qEEG abnormalities.

Systems and methods exist to measure the magneto elcephalogram (MEG) electromagnetic activity or magnetic fields arising from the flow of electrical currents within the brain which are proportional to the electroencephalographic activity. These magnetic fields can be used to detect brain abnormalities based on the measured activity. These magnetic fields are detected using data derived from superconductive quantum interference devices (SQUIDS) to detect spontaneous and or evoked electromagnetic activity correlated with brain electrical activity (EEG and or ERP) of an individual using one or more SQUID or MEG sensors placed near the scalp so as to detect the activity from selected regions of the brain.

Quantitative MEG ("qMEG") involves digital analysis of the MEG data, usually represented as a frequency spectrum evaluating the amount of activity of detected signals at the various frequencies represented in the MEG data Normative values as a function of age have not been established for the activity spectrum, but it is expected that such can be described and will be closely related to the qEEG normative data with respect to sensitivity and specificity to abnormality and to be independent of race, socio-economic status or ethnicity since the essentially the same neuroanatomical systems are responsible for generating both the MEG and the EEG signals. Using control data with the MEG similar differences have been described between individuals with normal and abnormal brain function as with the EEG in different categories of brain dysfunction.

An event-related potential ("ERP") is a recording of a neuroelectrical response of the brain to an event or stimulus. Changes in ERPs recorded from electrodes using EEG recording materials have been found to provide objective evidence of brain dysfunction relating to cognitive decline. Non-invasive ERP tests are available to measure brain activity during cognitive processing. ERP tests such as mismatch negativity (MMN) and P300 have been used to assess cognitive decline in a variety of areas including, for example, attention and memory. Similar tests may be performed using a variety of sensory events and paradigms. One such ERP test (P300) may include detecting a difference between an ERP elicited by a "common" (expected) event that occurs often in a sequence of repeated stimuli and ERP elicited by a rare (unexpected) event that is occasionally interspersed among the common (expected) ones. Another such test compares ERP's corresponding to pairs of stimuli where the first and second members of a pair are the same ('match') and where the second member of the pair is different from the first ('mismatch'). This type of test is known as MMN or mismatch negativity. Cognitive decline has been reported to correlate with the decrease in amplitude or disappearance and lengthening in latency of particular ERP components elicited by these tests. Another ERP test is known as the mid-latency auditory evoked response (MLAER) which examines the waveshape of electrical activity of the brain in response to tones or auditory clicks repeated for example at about 9/second. In the latency interval from about 6-8 milliseconds after stimulus delivery to approximately 50 milliseconds after stimulus delivery, certain components (e.g., $N_a$ and $P_b$) are known to be correlated with the storage of memory representing interactions between the midbrain and the cortex. Cognitive decline and memory deficit have been reported to correlate with the increase in amplitude or disappearance or lengthening in latency of particular ERP components elicited by these tests. The clinical assessment of the cognitive and functional capacity of individuals for their diagnoses and "staging" (to access the degree of impairment) may also rely upon neurocognitive ("NC") tests. NC tests have poor test-retest reliability in certain patient populations and are sometimes inaccurate or not useful with certain individuals because they depend to a large extent on the competence and experience of the person performing the assessment, as well as the language proficiency, educational attainment, active cooperation, and intelligence level of the individual. NC or other behavioral testing may not be useful where, for example, if the individual is depressed (or has other co-morbid disorders), disinterested in the test, has a short attention span or a low educational level. Abnormal performance on neurocognitive or behavioral measures does not necessarily reflect changes in the brain and at best are an indirect result of actual brain changes resulting from dementia. Furthermore, in people without signs of dementia (such as normal elderly) differences in NC tests are not sufficient to predict those persons likely to develop dementia from those who are unlikely to develop dementia.

Although methods exist to determine the existence of cognitive deterioration or decline, these methods do not enable the determination of an individual's potential for future cognitive decline. Although, the use of other imaging methods [e.g., Magnetic Resonance Imaging (MRI), Positron Emission Tomography (PET) and Single Proton Emission Computed Tomography (SPECT)] to detect abnormalities which may be predictive of future decline has been proposed, these tests are invasive, costly, lack normative data, depend on the skill of the person interpreting the data, can not be readily repeated at regular intervals and require special installations of large non-portable equipment.

Predictor algorithms are classifier functions which mathematically compute the probability that a set of features [such as those extracted from the qEEG and or qMEG and or ERP described in this application] are likely to belong to an individual from a particular group. Such algorithms may include, alone or in combination, multiple discriminant functions, regressions, cluster analyses or other classifier programs.

SUMMARY OF THE INVENTION

The present invention is directed to a system and method for prediction of cognitive decline, comprising an input receiving input data corresponding to brain activity of an individual and a processor coupled to the input for analyzing the input data to obtain a selected set of features, the processor comparing the selected set of features to at least a portion of entries in a database corresponding to brain activity of a plurality of individuals, wherein entries in the database have been separated into a plurality of categories corresponding to one of a degree of cognitive decline and a propensity for future cognitive decline of individuals relating to the entries, the processor determining, based on the comparison, a category most closely corresponding to the selected set of features.

Furthermore, the present invention is directed to a system and method for predicting cognitive decline comprising receiving input data corresponding to spontaneous brain electrical or other activity of an individual or brain responses activated by presentation of a variety of sensory stimuli or mental tasks. The input data which includes one of quantitative electroencephalogram data, quantitative magnetoencephalogram data and quantitative event related potential data is analyzed quantitatively by use of an analog to digital converter, digital amplifiers or any equivalent method to extract selected features therefrom and the selected features are compared to at least a portion of entries in a database including data corresponding to brain activity of a plurality of individuals. The entries in the database are separated into a plurality of categories corresponding to one of a degree of cognitive decline and a propensity for future cognitive decline of individuals relating to the entries and a category most closely corresponding to the input data is determined.

DETAILED DESCRIPTION

The present invention is directed to a system and method for the prediction of future cognitive decline. The system and method according to the present invention use quantitative electroencephalogram (qEEG) and/or quantitative magnetoencephalogram (qMEG) and/or quantitative event related potential (qERP) data to predict future cognitive decline in an individual. Unlike NC or neurobiological tests or other predictors used to determine present cognitive deterioration, the present invention predicts cognitive decline without the requirement of individual cooperation, is non-invasive, imposes no radio-active burden and accurate, objective results may be obtained by a skilled professional rather than the neurologist, psychiatrist, or neurophysiologist required by the any the other tests.

Figure 1:
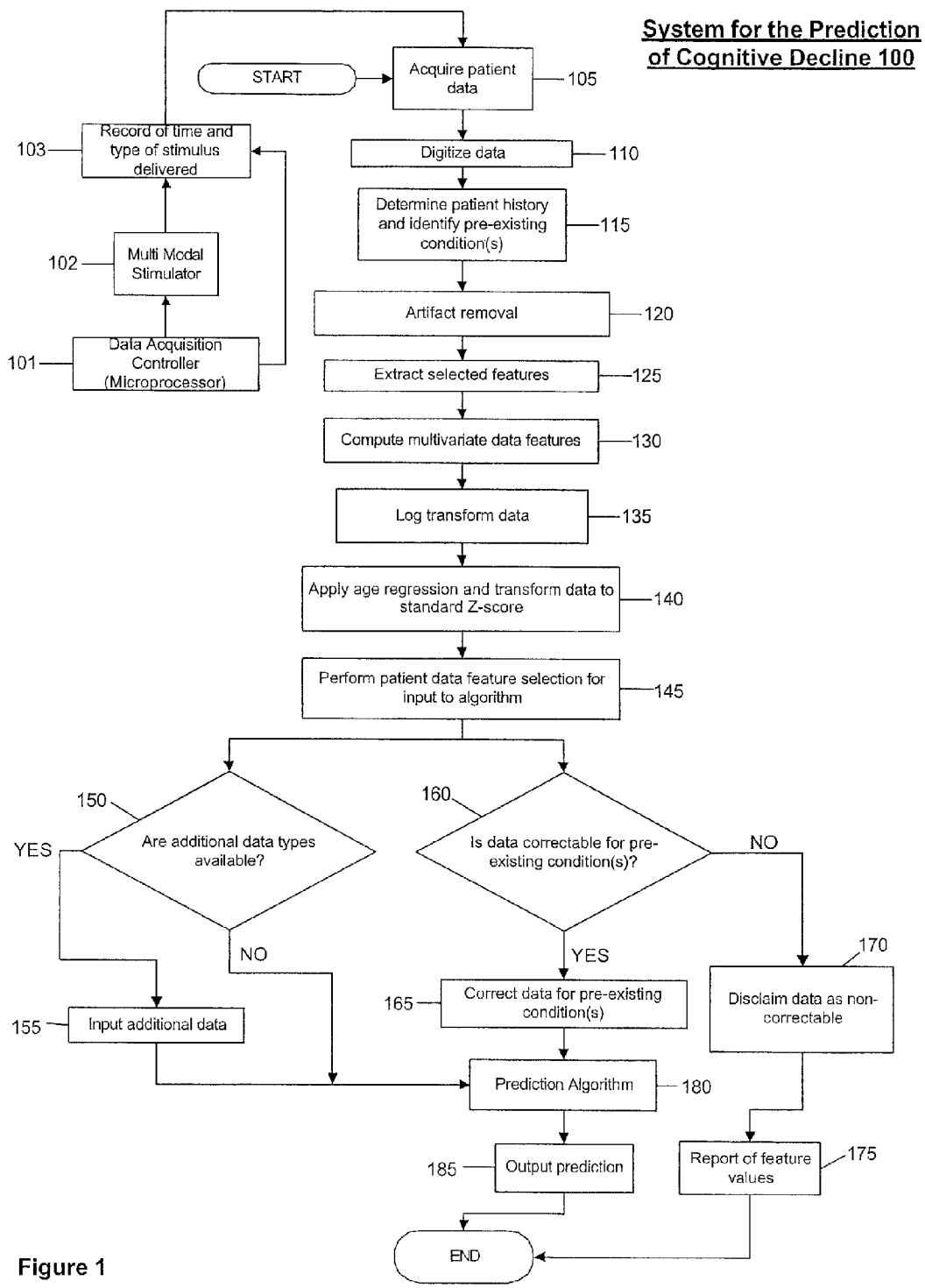
FIG. 1 shows a flow chart for an exemplary embodiment of a system for the prediction of cognitive decline according to the present invention.

FIG. 1 shows a flow chart of an embodiment of a system for the prediction of cognitive decline 100 according to the present invention. The system for the prediction of cognitive decline 100 includes a first step 105 of acquiring analog electroencephalogram ("EEG") and analog magnetoencephalogram ("MEG") and analog event-related potential ("ERP") data from an individual. A person skilled in the art will recognize that such quantification can be accomplished by digital as well as analog devices.

The EEG data may be acquired from the individual using a recording system according to the present invention. In one embodiment according to the present invention, the recording system includes a handheld, battery-powered device analogous to a FDA (personal digital assistant), which may also include EEG amplifiers. However, those skilled in the art will understand that a desktop device and a conventional electrophysiological system may be utilized for the recording system and that the power supply may be external as desired. The EEG amplifiers may, for example, have a band pass from 0.5 to 100 Hz or even as high as 1,000 Hz, or above (3 dB points) with a 60 Hz or 50 Hz notch filter. It is contemplated that digital EEG and MEG and ERP data may be acquired from the individual by any adequate electrophysiological data acquisition instrument or using any existing method and recording system.

The recording system preferably system preferably includes a set of electrodes (i.e., one or more), including for example, an array of electrodes positioned across or near the individual's forehead to sample bilateral prefrontal cortical regions (e.g. 10/20 positions: F7-F1-Fz-F2-F8), and or a midline frontal (Fz) and or a vertex (Cz) electrode and/or a parietal (Pz) electrode or bilateral parietal (P3 and P4) electrodes in addition to appropriate reference and ground leads. The recording system may further include a differential eye channel, or electrooculogram ("EOG"). As one of ordinary skill in the art would understand, EOG leads may be used to detect eye movement and may be diagonally placed above and below an eye orbit. Furthermore, as would be understood by those skilled in the art, SQUID MEG detectors may be used in a manner analogous to that described above for the electrodes.

While recording the EEG data, the individual may be, for example, seated in a sound and light attenuated testing chamber. A sample of eyes closed resting EEG data may first be collected, for example, from the 19 monopolar sites of the International 10/20 System, or from any preferred position (s), using silver/silver chloride or gel electrodes or other recording sensors referenced to linked earlobes or any preferred reference position. The electrode impedances are preferably below 5000 Ohms. A total sample of EEG data may be twenty (20) minutes, for example, but may be truncated if conditions require, for example, if artifact detection is performed on line or if any sample is shown to be usefully sensitive. A sample of, for example, 1-2 minutes of artifact-free EEG data will provide sufficient data. EEG data may be sampled at a rate of, for example, 200 Hz or higher with 12-bit to 16-bit resolution, or higher.

ERP data may be acquired in step 105 by any ERP test known to those of ordinary skill in the art which, for example, monitors the brain's response to a series of stimuli presented within a temporal or spatial flow structured to enable predictability. For example, the EEG and/or ERP data 105 may be acquired from the individual through the use of uni-modal or multi-modal (e.g. flash, sound, pictorial, verbal, cognitive, etc.) stimuli intended to provide data for mismatch-negativity ("MMN") and/or P300 components and or midlatency auditory evoked response ("MLAER") indexes. The ERP test may include, for example a MMN component and/or a P300 component and/or an MLAER component.

MMN includes, for example, the detection of a difference in brain electrical activity corresponding to samples of the responses elicited by two successive paired events, with the first sample including a period spanning a predetermined time (latency epoch) after presentation of the initial member of a pair of sequential stimuli and the second sample including a period spanning the same latency epoch or time interval after presentation of second member of the paired stimuli. That is, brain activity associated with processing these stimuli is expected after a predetermined neural processing delay and the activity measured during the first and second epochs is compared when both members of the pair are the same with respect to some dimension or attribute ("same-same") versus when the second member differs from the first ("same-different"). The ERP elicited by the two stimuli in the same-same pairs will be very similar while the ERP elicited by the second stimulus will differ from the ERP elicited by the first stimulus in the same-different pairs. Those skilled in the art will understand that the time between pairs may be the same as that between two events of a pair, or that the stimuli may be a continuous series of "same" events with randomly interspersed "different' events.

The P300 component may, for example, include the detection of a difference between the ERP elicited by an event that occurs often in a sequence of stimuli, preferably repeated at a slow rate (e.g. one per second), and a rare or oddball event that is occasionally interspersed among the common events. As one of ordinary skill in the art would understand, P300 may be a scalp-recorded voltage change elicited in response to infrequent, unpredictable, target stimuli occurring among frequent non-target stimuli. For example, in normally functioning individuals, a component known as P3A can be detected in anterior and posterior brain regions at a latency of about 200-225 ms after the presentation of the rare or oddball stimulus and a later component known as P3B may be detected in anterior, central or posterior regions at a latency of about 300 ms. These components differ from those elicited by the predictable, non-target or common stimuli. In impaired individuals with deficits of cognition, attention or working memory, P3A tends to disappear from anterior regions and P3B is delayed to appear at a latency of between 325 ms and 450 ms.

The MLAER component may be obtained by analyzing the waveshape of the ERP elicited by an auditory click or tone repeated in the range of for example 7-13 per second and recorded by volume conduction to electrodes or sensors placed for example on the mastoid or earlobes relative to one or many electrodes placed on the scalp or forehead. The waveshape of the MLAER, in the interval between the end of the auditory brainstem response and the first positive component of the auditory cortical evoked response (such as in the latency interval between 8 and 50 msec after the stimulus) relative to age expected values, contains a first negative ($N_a$) and a second positive ($P_b$) component. As one skilled in the art would know, the amplitude of $P_b$ reflects storage of memory and decreased amplitude and or increased latency reflect cognitive dysfunction.

The EEG and/or MEG and/or ERP data may be recorded in analog or digital format using the recording system according to the present invention. If the data is recorded in analog format, this data is digitized in step 110 and then, in step 120, may or may not be subject to artifacting or any other quality assurance procedure as would be understood by those skilled in the art. After this, in step 125 a selected set of features is extracted from the digital data of acceptable quality. In short, a selected set of features from the qEEG or qMEG or qERP data which are particularly relevant to assessment of cognitive decline are extracted from the overall data set obtained and compared to control data corresponding to brain activity of individuals in each of the various stages of cognitive decline or to brain activity of individuals known to have subsequently declined to generate a prediction as to the expected future cognitive evolution or decline of the individual. Thereafter, in steps 130 and 135, respectively, for EEG and/or MEG data (not for ERP data) univariate or multivariate (e.g., Mahalanobis distances) data features are computed for the extracted features and these features may be transformed (for example, log transformed) where appropriate to obtain a normal Gaussian distribution. As one skilled in the art will understand, the actual value of change or difference scores may alternately be used as criteria without these transforms or obtaining standard scores.

For example, in a first step of a procedure to extract the selected set of features, ANOVAS and other statistical methods are used to search out features "A" within the external EEG and/or MEG and/or ERP database (or other criterion values) which are significantly different between two or more groups of interest (such as normal compared with dementias and/or normal compared with stages of dementias or normal with and without future decline). Then, results from the first step, the set of features "A" are input to a multiple stepwise discriminant function the results of which will be used (a) as a classifier function itself to later be considered as part of the prediction strategy and/or (b) to reduce the number of features to a more sensitive set of features "B" to be entered into the next step which may include, for example, cluster analysis. The set of features "B' is input to a cluster analysis the results of which will be used (a) as a classifier function itself for later consideration as part of the prediction strategy and/or (b) to reduce the number of features to a more sensitive set of features "C" which may be used alone or in combination with the feature sets "A" and/or "B" as inputs to logistic regression. Similarly, a neural network may be used which receives as input a large unselected set of features extracted from the EEG and ERP and which outputs a reduced set of features "D" which can be used as a classifier function itself to later be considered as part of the prediction strategy and/or to reduce the number of features to a more sensitive set of features combined with the set of features "A" and/or the set of features "B" and/or the set of features "C" to be entered in the logistic regression.

Thereafter, as will be described in more detail below, the data is entered into the one or more classifier function(s) through which it is statistically associated with a subgroup representing individuals in similar or related states of cognitive decline within the database. Those skilled in the art will understand that, in place of the database, a look-up table or other structure representing similar data or other predefined criteria may be employed. For example, certain predictions may be made where a ratio of theta to alpha greater than 1.5 is detected in selected brain region(s). By applying a decision making CLASSIFIER FUNCTION such as regression to the individual's data the statistical likelihood that the individual will, at a time in the future, belong to a group with a specified degree of cognitive decline will be determined. The Regression module, the preferred embodiment being Logistic Regression, fits a common slope cumulative model, which is a parallel lines regression model, based on the cumulative probabilities of the response categories rather than on their individual probabilities. Taking into account k predictive variables for n individuals, the model is:

$$\text{Log}\ [p_i/1-p_i] = \alpha + \beta_1 x_{i1} + \beta_2 x_{i2} + \ldots + \beta_k x_{ik}$$

This equation which has been previously trained on the database including normally functioning individuals and patients at various stages of cognitive decline or those who displayed subsequent decline in a longitudinal follow-up is applied to the individual and a prediction is made. Those skilled in the art will understand that, in other embodiments any or a combination of discriminant functions, cluster algorithms, neural networks and/or other classifier functions will be applied to the data for the purpose of determining future group membership or cognitive decline.

Figure 2:
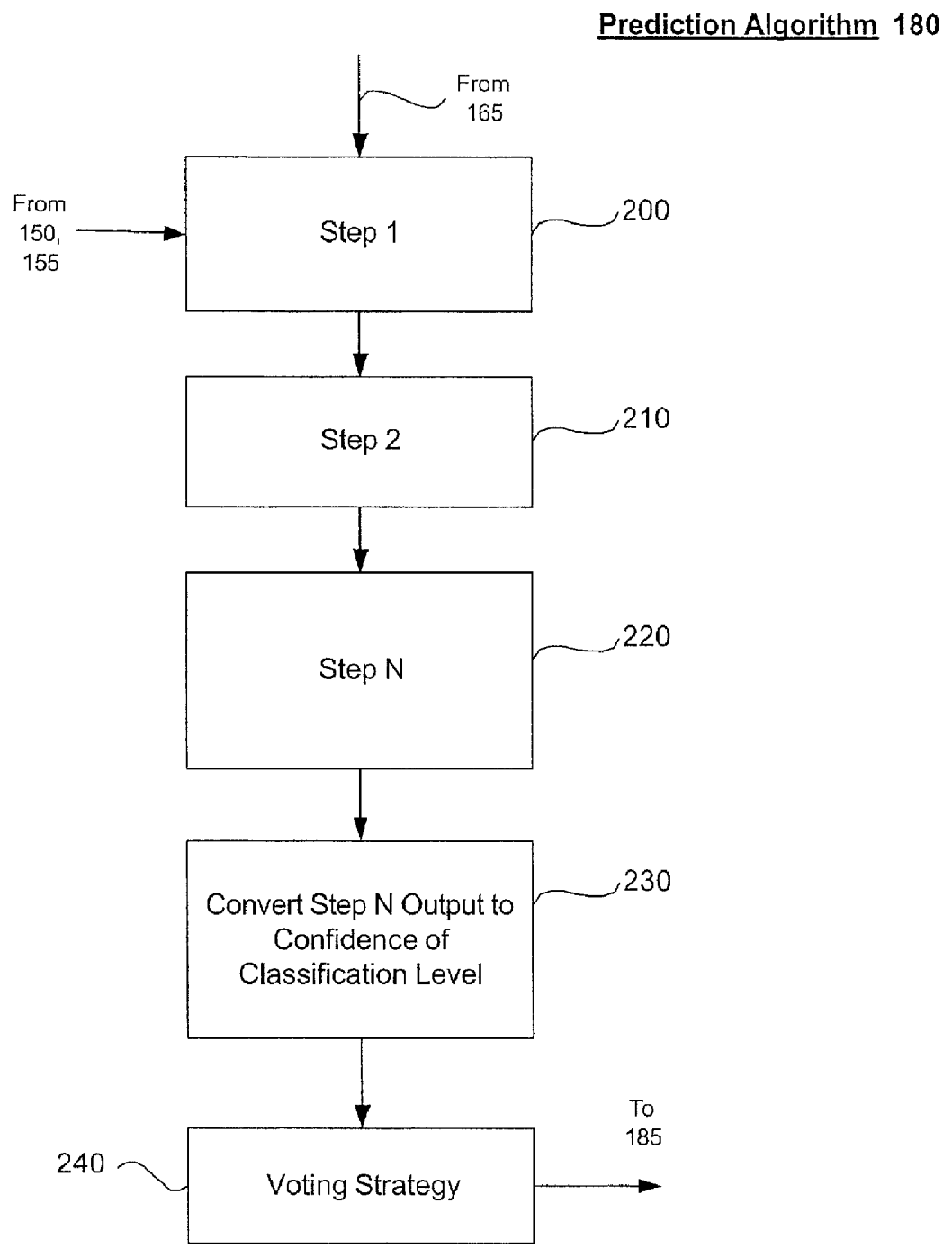
FIG. 2 shows a flow chart for an exemplary embodiment of a prediction algorithm according to the present invention.

Those skilled in the art will understand that, although the exemplary embodiment of the prediction algorithm described below specifically discloses steps for utilizing a Cluster Analysis module 400, a Discriminant Analysis module 500 and a Logistic Regression module, in that order, the prediction algorithm of the present invention may include some or all of these modules in any particular order. Furthermore, rules obtained by various other classifier modules, such as by using a neural network, may also be incorporated into the prediction algorithm 180 to generate a prediction of the expected cognitive decline of the patient. In addition, as one skilled in the art would understand, all of the modules utilized in the prediction algorithm 180 may be re-derived and/or modified following any or all changes to the database and improvements, refinements or future iterations of the classifier algorithms. However, in a preferred embodiment logistic regression is the final step in the procedure. For example, as shown in FIG. 2, in Step 1 (200) the selected features are input to a classification procedure such as, for example, a discriminant function to determine the relative probability of two or more states of cognitive decline which can be used to predict the probability ($P_1$) of future cognitive decline. The set of features identified in this analysis may also be input to other classifier functions such as cluster analysis and/or logistic regression.

For example, in Step 2 (210) the selected features are input to a classification procedure such as for example a cluster analysis to determine the relative probability of membership in two or more clusters reflecting different cognitive decline, membership in which can be used to predict the probability ($P_2$) of future cognitive decline; the set of features identified in this analysis can also be used as selected input to other classifier functions such as discriminant analysis and or logistic regression.

Then, in step N (220), selected features are input to, for example, a classification procedure such as a regression and/or logistic regression to determine the relative probability of two or more states of cognitive decline to predict a probability ($P_3$) of future cognitive decline. The set of features identified in this analysis may also be used as selected input to other classifier functions such as cluster analysis and/or discriminant function.

Thereafter, in step 230, the probability computed by the classification function of Step N is converted to a confidence level using Receiver Operating Characteristic (ROC) Curves as would be understood by those skilled in the art. Using plots of sensitivity versus specificity, the probability corresponding to various P levels (such as 0.10, 0.05, 0.01, etc.) may be specified. Where the results of multiple classifier functions are used to make the prediction of decline they may be combined using a "voting strategy" in Step 240 as would be understood by those skilled in the art. In addition, the prediction algorithm may utilize additional data (e.g., data concerning pre-existing conditions, clinical history/symptoms, neurobiological Or genetic information such as APOE) to further refine predictions.

In an exemplary embodiment according to the present invention, the recording system includes a stimulator cable and means for preprogrammed delivery of pairs or sequences of non-target ('same') or target ('different') stimuli in any selected modality or combination of modalities (e.g., tones of 90 db SL at any selected frequencies in either MMN or P300 paradigms or auditory clicks at the same intensity but with a repetition rate in the range of 7-11/second for the MLAER paradigm) for the collection of ERP data. Separate ERPs should be collected for the sample of "same" and of "different", with means for accurate registration of the type and time of delivery of each stimulus appropriately recorded upon one or more of the recording channels.

In certain patients, it may be considered feasible and desirable to focus attention and ensure compliance with instruction to attend to the sequence of "same" and "different" items by asking the subject to silently count the number of "different" or "target" items selected and inform the examiner of the final count when the ERP recording has been completed. Those skilled in the art will recognize that other methods of ensuring attention may be utilized, such as a finger press of a button to denote wither same, different, or either same or different finger responses. However, such cooperation is not necessary to obtain a P300 and a passive procedure of "same" and "different" items can be used.

Analog EEG data and/or MEG and/or ERP data and stimulus identification and timing information acquired in step 105 is digitized in step 110 to generate quantitative electroencephalogram ("qEEG") data and or quantitative magnetoencephalogram ("qMEG") and or quantitative event-related potential ("qERP") data. The EEG/MEG/ERP data may be digitized, for example, at 200 Hz with a 12-bit resolution or at 5 kHz with a 16-bit resolution, or at different sampling rates in different amplifier channels. Those skilled in the art will understand that it may be desirable to compute (Brain Stem Auditory Evoked Response) or BAER to confirm that the auditory system is adequately detecting the sensory stimuli.

In step 115 shown in FIG. 1, individual data corresponding to the individual's medical history and pre-existing conditions is assessed including data corresponding to, for example, audiological, visual, medical, neurological, psychiatric, pharmacological and neuropsychological evaluations conducted on the individual to determine whether a preexisting condition exists which could preclude or influence, or which should be incorporated into the interpretation of the qEEG/qMEG/qERP data.

If the individual data does not preclude further analysis, although not required a Global Deterioration Scale ("GDS") stage may have been determined for the individual clinically. GDS is based on age-associated decline of cognitive capacity and primary degenerative dementia. As one of ordinary skill in the art would understand, GDS stages one (1) and two (2) are normal elderly, stage three (3) corresponds to Mild Cognitive Impairment (MCI) and GDS stages four (4) to seven (7) are dementia stages of increasing severity. Individuals at GDS stage one have neither subjective nor objective evidence of cognitive decline, individuals at GDS stage two exhibit some subjective complaints of cognitive decline but no objective evidence of cognitive decline, and individuals at GDS stage three have mild cognitive decline objectively evidenced by memory deficiency, meeting criteria for MCI. Individuals in GDS stages four to seven have clear objective evidence of cognitive decline, classified as dementia with moderate cognitive decline in GDS stage four, moderately severe cognitive decline in GDS stage five, severe cognitive decline in GDS stage six, and very severe dementia in GDS stage seven. If available, such GDS scores should be included in the individual data in step 115. If available, such GDS scores, or scores from other similar staging methods, should be included in the individual data in step 115.

In a preferred embodiment of the present invention, additional neurocognitive (NC) testing of the individual is not required. However, additional NC tests may be performed to augment the qEEG and qMEG and qERP data. For example, a digit span or recall test (e.g. forward (DSF) and backward (DSB)) may be performed to test the longest sequence of numbers that an individual can recall. Further, a digit symbol substitution test ("DSST") may be performed to measure sensory-motor integration and learning relationships of symbols. As one of ordinary skill in the art will understand, such tests may include standardized subsets of the Wechsler Adult Intelligence Scale ("WAIS"). If available, DSF, DSB and WAIS scores should be included in the individual data in step 115.

In a preferred embodiment of the present invention, additional biological marker testing is not required. However, if available or easily acquired, additional biological data such as ApoE and or other genetic and or blood and or tissue markers may be used to augment the selected set of sensitive feature. Likewise, while not required, the selected set may be augmented with data from personal or familial historical and or demographic data such as age.

Alternatively, in the absence of artifact removal by the means described in section [00025], one might choose to use a method of test-retest validation and replication of non-artifacted or such edited data or a method which computes the means and standard deviations of features extracted from each of a set of successive short EEG segments and where data acquisition is considered adequate when these features converge to a stable value as the number of segments is increased. Any method which tracks the values of extracted features from such cumulative successive short EEG segment and assesses the statistically assesses the convergence to a stable estimate can be used.

As shown in FIG. 1, the system 100 for the prediction of cognitive decline preferably includes an artifact removal step 120. As one of ordinary skill in the art would understand, artifact removal 120, or artifacting, preferably includes the removal of artifacts or data attributable to extracerebral sources. Such artifacts may include, for example, data attributable to movement (e.g. body, head, electrode wires), eye blink or eye movement (e.g. eye movement detected by the EOG), swallowing, sweat or electro-dermal artifacts, and environmental artifacts (e.g. cell phones, lighting, dialysis pumps). The artifacting of step 120 is preferably performed by a computer algorithm to detect artifacts or non-stationarities or by visual inspection and editing of the qEEG/qERP data, augmented by a computerized artifact detection algorithm, amplitude driven, or by a computer algorithm to detect artifacts or non-stationarities and automatically exclude such artifacts from further analysis to ensure that qEEG/qERP data is not misinterpreted because of such artifacts or by use of methods such as "denoising" using wavelet analysis to improve the signal to noise ratio of the data.

In step 125, qEEG/qMEG/qERP features and relationships among such variables including significant and/or important predictors are extracted from the artifacted data. As one of ordinary skill in the art would understand, feature extraction techniques aggregate or combine predictors in a data sample in order to extract common information most useful for modeling the data sample.

In an exemplary embodiment according to the present invention, extracting qEEG/qERP features 125 includes a neurometric feature extraction method or Neurometrics. Those skilled in the art will understand that other data analysis methods such as, for example, wavelet analysis, nonlinear dynamic analysis, microstate analysis, etc. may be used to extract physiologically comparable descriptors of brain activity. A suitable Neurometric feature extraction method is described in the following publications which are expressly incorporated herein by reference in their entireties: John E R, Prichep L S, Friedman J, Easton P., Neurometrics: Computer assisted differential diagnosis of brain dysfunctions, *Science* 1988, 293, 162-169; John and Prichep chapter in Neidermeyer and Lopes da Silva Handbook of Electroencephalography, $3^{rd}$ Edition, 1993. The qEEG/qERP data is subjected to activity spectral analysis using a Fast Fourier Transform ("FFT"). As one of ordinary skill in the art would understand, FFT is a discrete Fourier transform algorithm which reduces the number of computations needed for N points from $2N^2$ to $2N \lg N$, where lg is a base-2 logarithm. For example, an absolute and relative (%) activity, mean frequency (a frequency within a band or across the spectrum at which half the activity lies above and half the activity lies below) for delta (1.5-3.5 Hz), theta (3.5-7.5 Hz), alpha (7.5-12.5 Hz) and beta (12.5-25 Hz) and gamma and ultra-high (25 Hz-1,000 Hz) frequency narrow band, broad band or sub-bands, and a total spectral activity may be computed for each of the 19 monopolar qEEG data sites for any subset sampled. As one of ordinary skill in the art would understand, relative activity is a percentage of the frequency band compared to the total activity over an entire 1.5-25 Hz or 1.5-1,000 Hz frequency range, or other total frequency band widths. Inter- and intra-hemispheric measures of the bispectra, coherence, covariance, symmetry, gradients, within, between and among regions may also be computed for any narrow band, broad band or sub-bands and total activity. Furthermore, as would be understood by those skilled in the art, the above-noted ranges for the various frequency bands are exemplary only and other ranges of these frequency bands (broad bands, narrow bands and/or sub-bands) are intended to be encompassed by each instance of these terms unless a specific range of frequencies is defined for a particular instance of the term. For example, when the alpha band is mentioned, although certain parties may define this band as encompassing frequencies between 7.5 to 12.5 Hz while others define it as encompassing 8 to 12 Hz, in the context of this application, the term alpha band encompasses all frequencies including broad bands, narrow bands and/or sub-bands thereof from the lowest, lower end of the alpha band to the highest of the higher ends of the accepted definitions of the alpha band.

Those skilled in the art will understand that Neurometric method also involves a Z-transform relative to age expected normal values from published, replicated and validated neurometric normative regression equations. This involves a transform where:

$$Z = \frac{\text{FEATURE IN THE INDIVIDUAL} - \text{AGE EXPECTED NORMAL VALUE}}{\text{STANDARD DEVIATION OF THE APPROPRIATE NORM}}$$

Or $$Z_{i,s} = \frac{Y_{i,s} - \hat{Y}(t_s)}{\sigma(t_s)}$$

Using The Z transform to age expected normal values allows a determination to be made as to which part of a feature reflects normal aging and which part lies beyond that expected due to normal aging.

Extraction of qERP features in step 125 may include the use of Spatial Principal Component Analysis (SPCA). Another exemplary embodiment according to the present invention may include a quantitative statistical assessment of the differences between two qERP data sets collected from the same individual. For example, a preferred method by which qERPs to common stimuli may be compared with qERPs to rare stimuli (or different members of pairs), is by computing the significance of the differences between values of two ERP samples at every time point Ti from the beginning to the end of the latency epoch (or a second element of a pair when it was the same versus different than a first element (MMN)). Two qERP data sets may be compared, a $qERP_1(t)$ and a $qERP_2(t)$, each comprising N samples of a time series of voltages beginning with an onset of two classes of stimuli. At every time point, or latency, in the two sets of qERP data, the sum of the voltages may be calculated, $\Sigma[V_1(t)]$ and $\Sigma[V_2(t)]$ and the sum of the voltages squared is also calculated as $\Sigma[V_1(t)]^2$ and $\Sigma[V_2(t)]^2$. A variance of each qERP data set at a latency t may then be computed using the following equations:

$$VAR_1 = \Sigma[V_1(t)]^2/N - (\Sigma[V_1(t)]/N)^2$$

$$VAR_2 = \Sigma[V_2(t)]^2/N - (\Sigma[V_2(t)]/N)^2.$$

A t-test for the significance of the difference between corresponding latencies t of the two qERP data sets may then be computed using the following equation:

$$T(t) = \{\Sigma[V_1(t)] - \Sigma[V_2(t)]\}/\{VAR_1 + VAR_2\}^{1/2}.$$

Signal enhancement of the qERP may be accomplished by a variety of methods such as optimum digital filtering or wavelet denoising to improve the signal to noise ratio. Preferably, the method for analysis of data from both qEEG and qERP will include assessment and confirmation of signal to noise ratio, signal quality and reliability using, for example, split half replication.

Those skilled in the art will understand that the same methodology may be employed with magnetic evoked potentials to obtain predictions in regard to cognitive decline substantially similar to that obtained through the use of electrical evoked potentials.

In steps 130, 135 and 140, after extraction of qEEG and qMEG and qERP features may be transformed for Gaussianity, and the construction of standard or Z-scores may be derived by comparing features obtained from the subject to values of healthy individuals obtained from a normative database [which is preferably external but may conceivably be stored within the instrument] accessible to the instruments, multivariate features such as Mahalanobis distances or square root of the sum of the squares may be computed which reflect relationships among neurophysiological processes and interactions among brain regions and which compress and reduce the data. Criteria to serve as thresholds to evaluate quantitative measurements without comparison to a reference database or standard score computation may also be used (such as a look-up table of values).

Selected qEEG and or qMEG and or qERP and or NC test scores and or other neurobiological or genetic data may be input to an assessment and prediction algorithm in Step 145. Such features may include or be combined into an overall brain state vector (BSV) defined as $BSV = [\Sigma Z^2 EEG + \Sigma Z^2 ERP + \Sigma Z^2 N \text{ other measures}]^{0.5}$. The BSV may be scaled as a standard or Z-score by methods well known in the art.

In step 150, the algorithm examines the individual data stored in 115 to ascertain whether additional data is available, e.g., qEEG/qMEG/qERP data from previous examinations, as well as other data such as GDS scores, NC test results, neurobiological data, genetic data, history of stroke or traumatic brain injury, medication with drugs likely to effect brain activity. If such data are available, they may be entered manually or preferably identified by interrogation of the individual data already stored in step 115. The addition of such data to the algorithm should occur and be confirmed in step 155.

If preexisting conditions have been identified, such as CNS active medication, stroke, or TBI history, in step 160 a determination is made as to whether the data is correctable to compensate for these factors. If yes, in step 165 appropriate conditions are applied (e.g., dual diagnosis algorithms, adjustments to compensate for known effects of pre-existing conditions, etc.).

Corrected data from step 165 and data not requiring correction from step 145 combined with additional data from step 155 are then entered into the prediction algorithm in step 180. If data are not correctable, a disclaimer of adequacy for prediction is invoked and all qEEG/qMEG/qERP features values and standard scores are provided as a report in step 175. In certain cases, alternative classifier functions may be applied to correct such data. For example, if a patient is taking a drug known to cause excess beta activity, an alternate classifier function may be used which does not rely on analysis of beta activity. Alternatively, data corresponding to the beta activity may be regressed out so that the data may be fed back into the original classifier functions.

If data have been unified and no corrections are required, the prediction, a confidence level and a report of all Z-scores for extracted qEEG/qMEG/qERP and NC test items are provided in step 185 to conclude the examination.

The individual data is then entered in a prediction algorithm 180, which has been previously constructed by applying to a relational database [which is preferably external but may conceivably be stored within the instrument] including if available NC data, neurobiological data, genetic data from a large number of normal individuals and patients in all of the stages of cognitive decline, one or more of discriminant functions, cluster analysis, other classifier functions and logistic regression. Each data entry in the database preferably includes at least one of brain activity data (e.g., qEEG/qMEG/qERP or other data corresponding to brain activity), features extracted from the brain activity data, multivariable features (e.g., Mahalanobis distances), NC tests, patient information (e.g., audiological, visual, medical, neurological, neurobiological, genetic, psychiatric, pharmacological, and neuropsychological evaluations), GDS stage (or other staging of cognitive decline), state of cognitive decline and probable future cognitive decline. Those skilled in the art will understand that this relational database may be constantly modified and updated as data is collected from each patient regarding his/her subsequent cognitive decline, etc., which may subsequently lead to future modifications/iterations of the classification algorithms implemented in the instrument.

As described above, a preferred embodiment of the prediction algorithm 180 is shown more clearly in FIG. 2. Individual data is entered into the one or more classifier function(s) through which it is statistically associated with a subgroup representing individuals in similar or related states of cognitive decline within the database. By applying a decision making CLASSIFIER FUNCTION such as regression to the individual's data the statistical likelihood that the individual will at a specified time in the future belong to a group with a specified degree of cognitive decline will be determined. The Regression module, the preferred embodiment being Logistic Regression, fits a common slope cumulative model, which is a parallel lines regression model, based on the cumulative probabilities of the response categories rather than on their individual probabilities. Taking into account k predictive variables for n individuals, the model is:

$$\text{Log } [p_i/1-p_i] = \alpha + \beta_1 x_{i1} + \beta_2 x_{i2} + \ldots + \beta_k x_{ik}$$

This equation which has been previously trained on the database including normally functioning individuals and patients at various stages of cognitive decline is applied to the individual and a prediction is made.

In another embodiment any or a combination of discriminant functions, cluster algorithms, neural networks and/or other classifier functions will be applied to the data for the purpose of determining future group membership or cognitive decline.

In any of the procedures enumerated above the output of the classifier function is a probability which is converted into a confidence level through the use of an ROC (receiver operating curve) strategy where plots of sensitivity versus specificity are used to extrapolate the confidence level (such as P<0.001) for any given predication probability as would be understood by those skilled in the art. As would be understood by those skilled in the art, regression analysis is a method for mathematically evaluating the relationship between a single criterion variable and a set of predictor variables. Logistic regression is the procedure of choice when the criterion variable is not continuous.

Figure 3:
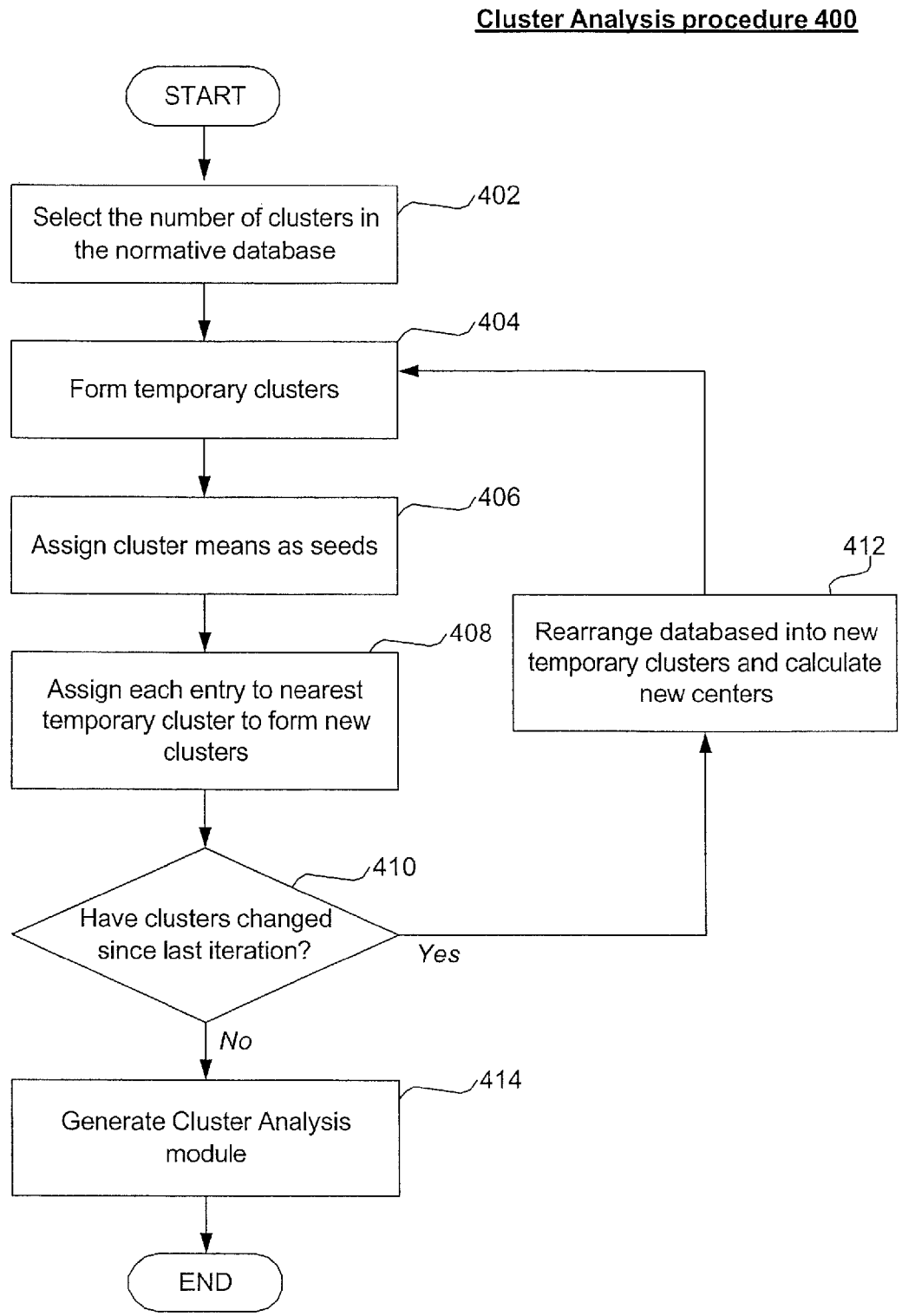
FIG. 3 shows a flow chart for an exemplary embodiment of a cluster analysis procedure used in developing a cluster analysis module utilized in the prediction algorithm.

FIG. 3 illustrates an exemplary cluster analysis procedure 400 for generating a Cluster Analysis module from the database. In step 402, the cluster analysis procedure is begun by determining a number of clusters desired. The optimal number of clusters (n) within a population can be defined by computation of the changes in the cluster structure as a function of n or set a priori based upon the number of clusters sought in the prediction model (for example, one for each GDS stage). Utilizing SAS FASTCLUS, for example, in step 404, k an initial "seed" is generated for each of the desired number of clusters and, in step 408 each entry in the database is assigned to the nearest "seed" based on its Euclidean distances to form temporary clusters. The "seeds" are then replaced by these temporary clusters. In step 412, new centers are determined for each of the temporary clusters and the process returns to step 406 where these new temporary clusters are assigned as "seeds" and the distances from the centers to each of the database entries are calculated and a new set of temporary clusters is with this entire procedure being iterated until, when in step 414 the clusters pass through the process with no further changes a cluster analysis module is generated for use in the prediction algorithm. Each individual is then classified using this cluster module to determine the probability that the patient is a member of a given one of the clusters. Those skilled in the art will understand that this clustering procedure is exemplary only and that a variety of alternative clustering methods may be used without departing from the scope of the invention.

Figure 4:
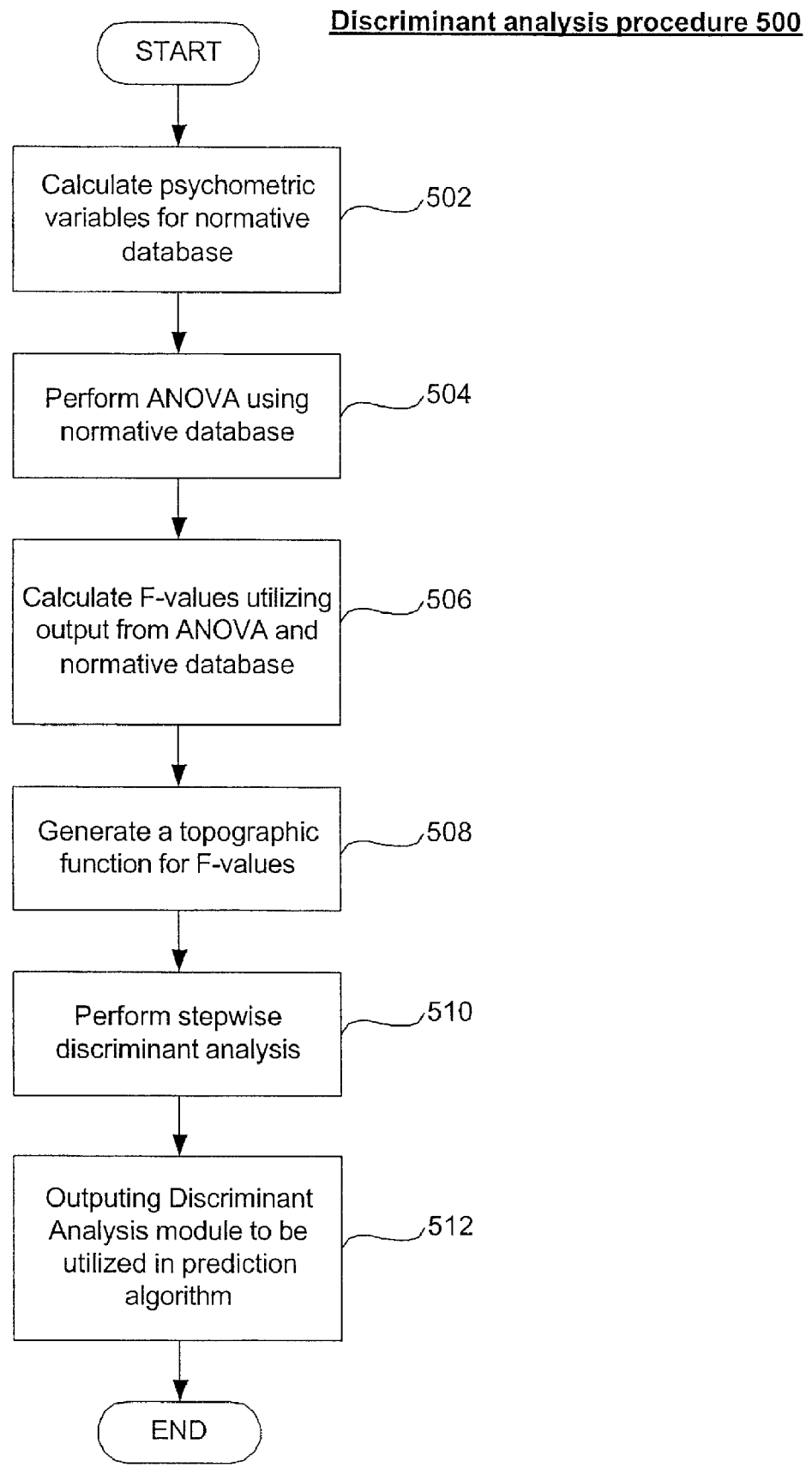
FIG. 4 shows a flow chart for an exemplary embodiment of a discriminant analysis procedure for developing a discriminant analysis module utilized in one embodiment of the prediction algorithm.

In one embodiment according to the invention, a Discriminant Analysis module 500, as shown in FIG. 4, is applied to the individual data to determine a probability that the individual most resembles or will resemble a particular stage of cognitive decline represented by the members of a particular cluster. The Discriminant Analysis module is generated based on the database, using a discriminant analysis procedure which may include at least one analysis of variance (ANOVA) procedure and a stepwise discriminant analysis procedure shown, as shown more clearly in FIG. 4.

Quantitative electrophysiological variables and other available variables, as raw values or transformed into standard or Z-scores, are calculated in step 502 to begin the discriminant analysis procedure 500. Univariate and/or multivariate Z-scores of the database are obtained in step 502 and step 504 subsequently utilizes the combined set of variables and performs at least one statistical procedure such as an ANOVA procedure. As would be understood by those skilled in the art, the ANOVA utilized in step 504 may be either of a one-way ANOVA and a multivariate analysis of variance (MANOVA) or a t-test or other tests of significance. Then, in step 506, F-values are calculated using output from the ANOVA and the database and a topographic function for the F-values is generated in step 508. After this a stepwise discriminant analysis is performed in step 510 and the discriminant analysis module is outputted in step 512.

The following represents an explanation of a one-way ANOVA procedure. However, it is contemplated that any ANOVA procedure or computer module known to those of ordinary skill in the art may be used for the analysis herein. As would be understood by those skilled in the art, the degree to which an outcome is predictable may be determined by applying a Logistic Regression module to the patient data which has previously been obtained by performing a logistic regression procedure on the database [which is preferably external but may conceivably be stored within the instrument]. More specifically, the logistic regression equation may be derived utilizing, for example, SAS/STAT Proc Logistic software provided by SAS Institute, Inc.

The logistic regression procedure fits a common slope cumulative model, which is a parallel lines regression model based on the cumulative probabilities of the response categories rather than on their individual probabilities. As one skilled in the art would understand, the Logistic Regression module may include an equation in the form of:

$$P_z = \frac{e^{\alpha + \beta 1 X 1 + \beta 2 X 2 + \ldots + \beta p X p}}{1 + e^{\alpha + \beta 1 X 1 + \beta 2 X 2 + \ldots + \beta p X p}}$$

where P is the probability of a particular outcome and Z is the liner function of $\alpha + \beta 1 X 1 + \beta 2 X 2 + \ldots + \beta p X p$. Estimated values for the parameters $\alpha, \beta 1, \beta 2, \ldots \beta p$ are obtained by a logistic regression module from the output generated in step 210 by the Discriminate Analysis module 500. Those skilled in the art will understand that for any of linear and non-linear models may be used.

Although the exemplary embodiment of the prediction algorithm illustrated in FIG. 2 specifically discloses steps for utilizing a Cluster Analysis module, a Discriminant Analysis module and a Logistic Regression module, in that order, the prediction algorithm of the present invention may include some or all of these modules in any particular order. Furthermore, rules obtained by various other classifier modules, such as by using a neural network, may also be incorporated into the prediction algorithm 180 to generate a prediction of the expected cognitive decline of the patient. In addition, as one skilled in the art would understand, all of the modules utilized in the prediction algorithm 180 may be re-derived and/or modified following any or all changes to the database and improvements, refinements or future iterations of the classifier algorithms.

As shown in FIG. 1, the prediction is outputted from the prediction algorithm in step 185. In short, a selected set of features from the qEEG or qMEG or qERP data which are particularly relevant to assessment of cognitive decline are extracted from the overall data set obtained and are compared to control data corresponding to brain activity of individuals in each of the various stages of cognitive decline or those known to have subsequent decline to generate a prediction as to the expected future cognitive evolution or decline of the individual.

It is contemplated that the system according to the present invention may be used by professionals to predict the cognitive decline of an individual without the use of NC or other imaging tests or subjective clinical evaluations. It might also evaluate cognitive improvement after treatment or be used to make a trajectory of evolution of decline over time. For example, the system according to the present invention may be used to evaluate elderly ambulatory individuals to determine the probability that their present cognitive capacity will improve, decline or remain relatively constant.

Particularly, the system according to the present invention may be used to predict potential for the future development of mild cognitive impairment ("MCI") and mild to severe Dementia of the Alzheimer's Type ("DAT") or other types of dementia. The system and method according to the present invention may be effective for individuals currently complaining of memory loss or who manifest some clinically overt evidence of dementia as well as for those who currently exhibit no symptoms of cognitive decline.

In another aspect, results of the prediction may be displayed graphically and/or numerically as embodied by, for example, a color-coded bar, a meter and a scale. The graph and/or scale may be used to provide a visual representation of the memory loss, dementia and/or cognitive decline. Similarly, the system may generate and display a trajectory corresponding to a longitudinal series of observations of the cognitive status of a patient or a predicted rate of cognitive decline over a predefined period of time. The expected cognitive decline may represent the predicted probabilities over multiple longitudinal evaluations of the patient during a follow-up period. The trajectory may be useful in prescribing treatment.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention, including a variety of possible statistical or other methods to identify qEEG/qMEG/qERP variables or other measures corresponding to brain activity to define the prediction algorithm, for example, neural networks, bispectral or spectral analysis, wavelet analysis, chaos analysis, fractal analysis, principal component analysis, independent component analysis, singular value decomposition, microstate distributions, microstate transition probabilities and global field synchrony. Only the ability to extract the sensitive variables and apply them to the algorithms previously computed need be provided in the device for the preferred embodiment.

Furthermore, those skilled in the art will understand that, while this application describes electrodes placed on the scalp to detect brain activity, this is in no way to be construed as the only way such data may be collected for use in a system or method according to the present invention. Rather, this invention contemplates receiving and processing data from any source outside or inside the body and even within the brain itself. And, as components are further minimized certain components of this system which are described as located outside the body may be components of data gathering or other structures which reside within or which are temporarily introduced into the body. In addition, the components described for converting the input data to a series of quantitative values may include any of an analog/digital converter, a digital amplifier or any other structure which performs this function. The specific hardware employed is not critical to the functioning of this invention.

In addition, those skilled in the art will understand that there are other measures, for example, including measures of blood flow through and/or oxygen consumption in various regions of the brain may be positively or negatively correlated to brain activity. Thus measures of these or other parameters corresponding to brain activity may also be used in accord with the method and system of the invention.

What is claimed is:

1. A method for prediction of cognitive decline of a patient during a future time period, comprising:
receiving input data corresponding to electrical brain activity of an individual;
analyzing, using a processor, the input data to extract selected features therefrom;
comparing, using the processor, the selected features to at least a portion of entries in a database, the database including data corresponding to brain activity of a plurality of individuals, wherein entries in the database are separated into a plurality of categories corresponding to a degree of cognitive decline of the individuals when the data corresponding to brain activity was collected and a degree of cognitive decline of the individuals during a period of time subsequent to the collection of data corresponding to brain activity; and
determining, using the processor, a category of the plurality of categories most closely corresponding to the input data.

2. The method according to claim 1, wherein the input data includes one of quantitative electroencephalogram data, quantitative magnetoencephalogram data and quantitative event related potential data.

3. The method according to claim 1, wherein the categories correspond to rankings on a clinical staging scale.

4. The method according to claim 3, wherein the clinical staging scale is a Global Deterioration Scale (GDS).

5. The method according to claim 1, wherein the input data includes ERP data corresponding to time frames immediately after presentation of a series of stimuli presented in one of a plurality of sensory modalities, a plurality of sensory attributes and a plurality of stimulus attributes within a single sensory modality, including common stimuli and at least one of rare and novel stimuli, a difference being determined between ERP associated with common stimuli and ERP associated with the at least one of rare and novel stimuli.

6. The method according to claim 5, wherein, for each of a plurality of pairs of stimuli, the first set of data corresponds to a first time frame $ERP_1$ immediately after presentation of a first member of one of the pairs of stimuli and a second set corresponds to a second time frame $ERP_2$ immediately after presentation of a second member of one of the pairs of stimuli, wherein, for each of a first portion of the pairs of stimuli, the second member is the same as the first member and, for each of a second portion of the pairs of stimuli, the second member is different from the first member, $ERP_1$ and $ERP_2$ being compared to one another for each of the first and second portions of the pairs of stimuli.

7. The method according to claim 1, wherein the selected features are augmented based on scores from a neurocognitive testing assessment.

8. The method according to claim 1, wherein the selected features are augmented based on scores from a neurobiological marker assessment.

9. The method according to claim 8, wherein the neurobiological marker assessment is one of ApoE and scores derived from clinical historical data.

10. The method according to claim 5, further comprising computing a t-test to assess a significance of a difference between latency periods following presentation of common stimuli and latency periods following the presentation of the at least one of rare and novel stimuli.

11. The method according to claim 10, wherein the latency periods include time periods from 200 to 250 ms and 275 to 350 ms after presentation of the corresponding stimulus.

12. The method according to claim 5, in which stimuli are presented in one of a plurality of sensory modalities and a plurality of stimulus types to a single sensory modality.

13. The method according to claim 6, wherein a preceding time frame immediately after presentation of each of a plurality of individual stimuli is compared to a corresponding time frame immediately after presentation of a succeeding stimulus, with a first portion of comparisons being made for a case where the succeeding stimulus is different from an immediately preceding stimulus and a second portion of the comparisons being made for a case where the succeeding stimulus is the same as the immediately preceding stimulus.

14. The method according to claim 6, wherein $ERP_1$ and $ERP_2$ include time intervals approximately 100 to 230 ms after presentation of the corresponding stimulus.

15. The method according to claim 1, wherein the selected features include data corresponding to one of absolute and relative brain wave activity in a delta band.

16. The method according to claim 1, wherein the selected features include data corresponding to one of absolute and relative brain wave activity in a theta band.

17. The method according to claim 1, wherein the selected features include data corresponding to one of absolute and relative brain wave activity in an alpha band.

18. The method according to claim 1, wherein the selected features include data corresponding to one of absolute and relative brain wave activity in a beta band.

19. The method according to claim 1, wherein the selected features include data corresponding to one of absolute and relative brain wave activity in a gamma band.

20. The method according to claim 1, wherein the selected features include data corresponding to one of absolute and relative brain wave activity in an ultra-high frequency band.

21. The method according to claim 20, wherein the ultra-high frequency band includes frequencies ranging from 50 Hz to 1,000 Hz.

22. The method according to claim 1, wherein the selected features include data corresponding to one of brain wave absolute and brain wave relative delta plus theta activity.

23. The method according to claim 1, wherein the selected features include data corresponding to theta spectral activity in posterior and parietal regions and delta spectral power in prefrontal, mesial and frontal regions.

24. The method according to claim 22, wherein the data corresponding to theta spectral activity and delta spectral activity includes a multivariate combination of measurements within these frequency bands based on input from one of the prefrontal and mesial frontal regions.

25. The method according to claim 22, wherein the data corresponding to theta spectral activity and delta spectral activity includes a multivariate combination of measurements within these frequency ranges based on input from one of the frontal, posterior temporal, parietal and occipital regions.

26. The method according to claim 1, wherein the selected features include data corresponding to voltage gradients of activity between and among brain regions.

27. The method according to claim 1, wherein the selected features include one of univariate data features extracted from one of EEG data and MEG data, multivariate data features extracted from one of EEG data and MEG data, Mahalanobis distances extracted from one of EEG data and MEG data and ERP data corresponding to time frames immediately after presentation of a series of stimuli presented in one of a plurality of sensory modalities, a plurality of sensory attributes and a plurality of stimulus attributes within a single sensory modality, including common stimuli and at least one of rare and novel stimuli, a difference being determined between ERP associated with common stimuli and ERP associated with the at least one of rare and novel stimuli.

28. The method according to claim 27, further comprising the step of log transforming the selected features to obtain a normal Gaussian distribution.

29. The method according to claim 1, further comprising the step of removing from the input data one or both of artifacts and data attributable to extracerebral sources.

30. The method according to claim 1, further comprising the step of predicting an expected trajectory of the cognitive state of the individual in a future time period.

* * * * *